US012582686B2

(12) United States Patent
Hwang

(10) Patent No.: US 12,582,686 B2
(45) Date of Patent: Mar. 24, 2026

(54) MANUFACTURING METHOD FOR COMPOSITION PROMOTING RECOVERY OF BONE FRACTURE

(71) Applicant: Man Ki Hwang, Seoul (KR)

(72) Inventor: Man Ki Hwang, Seoul (KR)

( * ) Notice: Subject to any disclaimer, the term of this patent is extended or adjusted under 35 U.S.C. 154(b) by 347 days.

(21) Appl. No.: 18/390,276

(22) Filed: Dec. 20, 2023

(65) Prior Publication Data

US 2024/0216451 A1 Jul. 4, 2024

(30) Foreign Application Priority Data

Dec. 29, 2022 (KR) ........................ 10-2022-0188400

(51) Int. Cl.
| | |
|---|---|
| *A61K 36/232* | (2006.01) |
| *A61K 36/126* | (2006.01) |
| *A61K 36/234* | (2006.01) |
| *A61K 36/324* | (2006.01) |
| *A61K 36/328* | (2006.01) |
| *A61K 36/344* | (2006.01) |
| *A61K 36/481* | (2006.01) |
| *A61K 36/53* | (2006.01) |
| *A61K 36/752* | (2006.01) |
| *A61K 36/9064* | (2006.01) |
| *A61P 19/00* | (2006.01) |

(52) U.S. Cl.
CPC .......... *A61K 36/232* (2013.01); *A61K 36/126* (2013.01); *A61K 36/234* (2013.01); *A61K 36/324* (2013.01); *A61K 36/328* (2013.01); *A61K 36/344* (2013.01); *A61K 36/481* (2013.01); *A61K 36/53* (2013.01); *A61K 36/752* (2013.01); *A61K 36/9064* (2013.01); *A61P 19/00* (2018.01); *A61K 2236/15* (2013.01); *A61K 2236/333* (2013.01)

(58) Field of Classification Search
CPC .. A61K 36/232; A61K 36/126; A61K 36/234; A61K 36/324; A61K 36/328; A61K 36/344; A61K 36/481; A61K 36/53; A61K 36/752; A61K 36/9064; A61K 2236/15; A61K 2236/333; A61K 2236/33; A61K 2236/39; A61P 19/00
See application file for complete search history.

(56) References Cited

FOREIGN PATENT DOCUMENTS

| | | | | | |
|---|---|---|---|---|---|
| CN | 101239172 A | * | 8/2008 | | |
| KR | 10-2004-0007596 A | | 1/2004 | | |
| KR | 102355277 B1 | * | 1/2022 | ............. | A61P 19/08 |
| KR | 10-2587602 B1 | | 10/2023 | | |

OTHER PUBLICATIONS

KR-102355277-B1, translation, 8 pages. (Year: 2022).*
CN-101239172-A, translation, 4 pages. (Year: 2008).*
Notice of Preliminary Examination Result issued from Korean Patent Application No. 10-2022-0188400 issued on Feb. 6, 2023.

* cited by examiner

*Primary Examiner* — Aaron J Kosar
*Assistant Examiner* — Jennifer Lynn Cain
(74) *Attorney, Agent, or Firm* — Sughrue Mion, PLLC

(57) ABSTRACT

Disclosed herein is a method for manufacturing a composition promoting recovery from a bone fracture, the method including preparing a mixture of *Angelica gigas, Cnidium officinale, Phlomis umbrosa, Astragalus membranceus, Amomi fructus, Citri unshius pericarpium, Drynariae Rhizoma, Codonopsis Pilosulae Radix,* frankincense, and myrrh, aging the mixture, smoking the mixture, drying the mixture and grinding the dried mixture into a powder, and extracting a liquid from the powder.

4 Claims, No Drawings

MANUFACTURING METHOD FOR COMPOSITION PROMOTING RECOVERY OF BONE FRACTURE

CROSS-REFERENCE TO RELATED APPLICATION

This application claims priority to and the benefit of Korean Patent Application No. 2022-0188400, filed on Dec. 29, 2022, the disclosure of which is incorporated herein by reference in its entirety.

BACKGROUND

1. Field of the Invention

The present disclosure relates to a method for manufacturing a composition promoting recovery from a bone fracture, and more particularly, to a method for manufacturing a composition that promotes bone fracture recovery and provides enhanced sweetness using a mixture containing *Angelica gigas, Cnidium officinale, Phlomis umbrosa, Astragalus membranceus, Amomi fructus, Citri unshius pericarpium, Drynariae Rhizoma, Codonopsis Pilosulae Radix*, frankincense, and myrrh, such that the composition can be easily consumed by various age groups.

2. Description of the Related Art

A bone fracture is the breakdown of a bone in a part of the body. Bone fractures are affected by a number of physical and biological factors, and can be healed by the formation of new tissue around the bone fracture and the joining of the two separated bones.

Various methods have been proposed to promote recovery from bone fractures, including slowing venous flow, cutting sympathetic nerves, providing electrical stimulation, administering hormones, or giving specific compounds, such as vitamin D, vitamin D derivatives, calcitonin, and BMPs.

However, satisfactory bone fracture healing methods or bone fracture treatment drugs have not yet been developed.

In general, the treatment method for bone fractures caused by physical external forces is to perform a surgical operation and then fix the bone with a splint or plaster bandage to allow the bone to heal naturally. However, in the case of this treatment method, the recovery period of the bone fracture is long and side effects may occur on the internal state of the bone.

PRIOR ART LITERATURE (Patent Document 1) Korean Patent Application Publication No. 10-2004-0007596 (Jan. 24, 2004)

SUMMARY OF THE DISCLOSURE

Therefore, the present disclosure has been made in view of the above problems, and it is an object of the present disclosure to provide a method for manufacturing a composition promoting recovery from a bone fracture that reduces the period of bone fracture recovery, activates osteoblast proliferation, and induces bone regeneration, while providing improved flavor.

In accordance with the present disclosure, the above and other objects can be accomplished by the provision of a method for manufacturing a composition promoting recovery from a bone fracture, the method including preparing a mixture of *Angelica gigas, Cnidium officinale, Phlomis umbrosa, astragalus membranceus, Amomi fructus, Citri unshius pericarpium, Drynariae Rhizoma, Codonopsis Pilosulae Radix*, frankincense, and myrrh, aging the mixture, smoking the mixture, drying the mixture and grinding the dried mixture into a powder, and extracting a liquid from the powder.

According to one embodiment, the composition may contain 10-15 parts by weight of *Angelica gigas*, 10-15 parts by weight of *Cnidium officinale*, 5-7 parts by weight of *Phlomis umbrosa*, 10-15 parts by weight of *astragalus membranceus*, 5-10 parts by weight of *Amomi fructus*, 5-10 parts by weight of *Citri unshius pericarpium*, 5-10 parts by weight of *Drynariae Rhizoma*, 1-5 parts by weight of *Codonopsis Pilosulae Radix*, 1-5 parts by weight of frankincense, and 1-5 parts by weight of myrrh.

According to one embodiment, the aging of the mixture may include adding 5-10 parts by weight of the rice spent water to the mixture, and aging the mixture at a temperature of 40° C. for 10 hours.

According to one embodiment, the smoking of the mixture may include smoking the mixture at a temperature of 80° C. for 2 hours using smoke from burning of 5-10 parts by weight of the cherry wood.

According to one embodiment, the extracting of the liquid from the powder may include adding 5-10 weight parts of ethanol to the powder as a solvent, and repeatedly performing the extraction 6 times at a temperature of 60° C. for 2 hours by applying 20-30 kHz ultrasonic waves.

DETAILED DESCRIPTION OF THE DISCLOSURE

Hereinafter, specific details for practicing the present disclosure are described in detail. However, in the following description, detailed descriptions of widely known functions or configurations are omitted to avoid obscuring the main points of the present disclosure unnecessarily.

The terms used in this specification will be briefly described, and then embodiments of the present disclosure will be described in detail. Although the terms used in this specification are selected, as much as possible, from general terms that are widely used at present while taking into consideration the functions obtained in accordance with at least one embodiment, these terms may be replaced by other terms based on intentions of those skilled in the art, judicial precedent, emergence of new technologies, or the like. Additionally, in a particular case, terms that are arbitrarily selected by the applicant may be used. In this case, meanings of these terms will be disclosed in detail in the corresponding description of the present disclosure. Accordingly, the terms used herein should be defined based on practical meanings thereof and the whole content of this specification, rather than being simply construed based on names of the terms.

A singular expression includes a plural expression unless the context clearly dictates otherwise. In addition, plural expressions include singular expressions unless the context clearly indicates that they are plural.

Throughout this specification, when a part "includes" a component, it means that the part may further include other components, rather than excluding the other components, unless otherwise stated.

As used throughout this specification, the terms "approximately," "substantially," and the like are intended to be inclusive of tolerances when tolerances exist.

Throughout this specification, the term "combination(s) thereof" as used in a Makushi-style expression means a mixture or combination of one or more selected from a group of components described in the Makushi-style expression.

Throughout this specification, references to "A and/or B" shall mean "A, or B, or A and B".

Hereinafter, embodiments of the present disclosure will be described in detail so that those skilled in the art can easily practice the present disclosure. The present disclosure may, however, be embodied in many different forms and should not be construed as limited to the embodiments set forth herein.

A method for manufacturing a composition promoting recovery from a bone fracture according to one embodiment of the present disclosure includes preparing a mixture of *Angelica gigas, Cnidium officinale, Phlomis umbrosa, astragalus membranceus, Amomi fructus, Citri unshius pericarpium, Drynariae Rhizoma, Codonopsis Pilosulae Radix*, frankincense, and myrrh, aging the mixture, smoking the mixture, drying and grinding the mixture into a powder, and extracting a liquid from the powder.

According to one embodiment of the present disclosure, the method for manufacturing a composition promoting recovery from a bone fracture includes preparing a mixture of *Angelica gigas, Cnidium officinale, Phlomis umbrosa, astragalus membranceus, Amomi fructus, Citri unshius pericarpium, Drynariae Rhizoma, Codonopsis Pilosulae Radix*, frankincense and myrrh.

The composition according to the present disclosure contains 10-15 parts by weight of *Angelica gigas*, 10-15 parts by weight of *Cnidium officinale*, 5-7 parts by weight of *Phlomis umbrosa*, 10-15 parts by weight of *astragalus* membranceus, 5-10 parts by weight of *Amomi fructus*, 5-10 parts by weight of *Citri unshius pericarpium*, 5-10 parts by weight of *Drynariae Rhizoma*, 1-5 parts by weight of *Codonopsis Pilosulae Radix*, 1-5 parts by weight of frankincense, and 1-5 parts by weight of myrrh.

The composition according to the present disclosure contains 10-15 parts by weight of *Angelica gigas*.

The *Angelica gigas* according to the present disclosure is the dried root of *Angelica gigas* Nakai, which belongs to the Umbeliferae, and contains a large amount of coumarin components in various forms such as decursin, decursinol, nodakenetin, umbelliferone, nodakenin, xanthotoxin, isopimpinellin, and ostol, which have excellent antioxidant activity and are used for the prevention and treatment of various diseases as they improve blood circulation, and have analgesic effect, hematopoietic effect, anti-inflammatory effect, etc.

In addition, the ability of *Angelica gigas* to proliferate bone cells has already been reported (Journal of Biopharmacology 40(3): 190-195 (2009), Activity of Medicinal Plants on Proliferation and Differentiation of Osteoblasts). *Angelica gigas* directly stimulates bone cell proliferation, alkaline phosphatase (ALP) activity, and protein secretion.

Leaves, shoots or roots of *Angelica gigas* according to the present disclosure may be used. Preferably, the roots are used.

The composition according to the present disclosure contains 10-15 parts by weight of *Cnidium officinale*.

*Cnidium officinale* according to the present disclosure, which is a perennial herb of the of the dicotyledonous plant, Umbrella family, Apiaceae, contains a large amount of alkaloids (Tetramethylpyrazine, Perolyrine), phenolic components (Chrysophanoll, Sedanonic acid), lactones, and vitamin E. Thus, it exhibits excellent antioxidant activity and is used for the prevention and treatment of various diseases due to its analgesic, tonic, antibacterial, anti-inflammatory, and immune-enhancing effects.

*Cnidium officinale* does not have a direct effect on bone fractures, but exerts an effect on inflammation, which further promotes recovery from bone fractures.

Leaves, stems or roots of *Cnidium officinale* according to the present disclosure may be used. Preferably, the roots are used.

The composition according to the present disclosure contains 5-7 parts by weight of *Phlomis umbrosa*.

*Phlomis umbrosa* according to the present disclosure, which refers to the root of the harebell, a perennial herbaceous plant belonging to the harebell family, has a useful effect on growth hormone secretion and growth promotion.

Currently known pharmacological effects of *Phlomis umbrosa* include antidiabetic effect, muscle and joint pain relief, anti-complementary effect, treatment of cough, phlegm, asthma and diarrhea due to low physical strength. *Phlomis umbrosa* is used for arthritis, premature ejaculation, and anemia by strengthening muscles and bones, communicating blood vessels, and supporting the liver and kidney functions.

Young leaves and roots of *Phlomis umbrosa* according to the present disclosure may be used. Preferably, the roots are used.

The composition according to the present disclosure contains 10-15 parts by weight of *astragalus membranceus*.

The major components of *astragalus membranceus* according to the present disclosure include triterpenoids, isoflavonoids, and polysaccharides. The isoflavonoids contain formononetin and calycosin. The isoflavonoids are phytoestrogens, which are known to be a natural alternative to female sex hormones.

The leaves, shoots or roots of *astragalus membranceus* according to the present disclosure can be used, preferably the roots.

*Astragalus membranceus* regulates the amount of sweat and has a diuretic effect, and is therefore a good medicine for obese people as a treatment for diabetes. *Astragalus membranceus* is effective in preventing sweating, strengthening the skin, draining pus, reducing swelling, and granulating. *Astragalus membranceus* is also effective in relieving chronic fatigue, treating insomnia, and improving a weak constitution.

Since *astragalus membranceus* expands skin blood vessels, it helps blood circulation. Also, because it increases the resistance of capillaries, stragalus membranceus helps blood circulation around the bone fracture area, thereby enabling the human body to recover from bone fractures.

The composition according to the present disclosure contains 5-10 parts by weight of *Amomi fructus*.

*Amomi fructus* according to the present disclosure generally refers to the fruit of a perennial herbaceous plant belonging to the ginger family. It contains 1.7 to 3% of aromatic essential oil as its effective medicinal component. The main components are d-camphor, d-boneol, bornyl acetate, linalol, and neroldal, and are effective for promotion of gastrointestinal motility, gastric ulcer, smooth muscle relaxation, pain relief, vomiting, diarrhea, dysentery, pregnancy vomiting, loss of appetite, indigestion, and dyspepsia related to muscle tension and food.

The *Amomi fructus* according to the present disclosure is preferably an extract obtained from the fruit or part of the fruit of the perennial herbaceous plant *Amomi fructus* or its congeners, or from materials derived therefrom.

The composition according to the present disclosure contains 5-10 parts by weight of *Citri unshius pericarpium.*

*Citri unshius pericarpium* according to the present disclosure refers to tangerine peels that have been aged for one to three years and contains essential oil, citric acid, vitamin A, vitamin B1, D-calactosamine, vitamin C, hesperidin, beta-cryptoxanthin, and salpesterol, turpentine, etc. It is effective in improving liver function, improving chronic fatigue, enhancing physical strength, restoring energy, preventing cancer, preventing aging, preventing inflammation, reducing inflammation, treating bronchial diseases, preventing cardiovascular diseases, increasing immunity, and enhancing skin beauty. In particular, the beta-cryptoxanthin in *Citri unshius pericarpium* strengthens bones and helps prevent bone fractures.

The composition according to the present disclosure contains 5-10 parts by weight of *Drynariae Rhizoma.*

The *Drynariae Rhizoma* according to the present disclosure refers to the underground stem of *Davallia mariesii* and contains enzyme components such as alkaline photophosphatase and prolyl hydroxylase as its main components, which increase the thickness of bones and skin, relieve pain in the back and knees, and are beneficial for bone-related diseases such as osteoporosis, bone metabolic diseases, fusion of bone fractures, and growth promotion. *Drynariae Rhizoma* also contains hesperidin, which has an antioxidant effect and is effective in discharging harmful free radicals, protecting capillaries, and preventing cardiovascular diseases such as hypertension, hyperlipidemia, and arteriosclerosis.

The composition according to the present disclosure contains 1-5 parts by weight of *Codonopsis Pilosulae Radix.*

*Codonopsis Pilosulae Radix* according to the present disclosure is the dried root of *Codonopsis pilosula*, a plant belonging to the bellflower family, and contains saponin, trace alkaloids, sucrose, glucose, inulin, starch, mucilage, resin, etc. The root contains essential oil, scutellarein glucoside, alkaloids, polysaccharides, inulin, saponin, etc. and is used to treat anorexia, dipsesis, hderocele, etc.

The composition according to the present invention contains 1-5 parts by weight of frankincense.

Frankincense according to the present disclosure is an aromatic medicinal product made by drying the sap of the frankincense tree of the olive family. The substance boswellic acid contained in frankincense increases the survival rate of chondrocytes and has an excellent protective effect on cartilage, inhibiting inflammation and improving blood circulation to reduce joint pain.

The composition according to the present disclosure comprises 1-5 parts by weight of myrrh.

The myrrh according to the present disclosure is a medicinal product made by drying the fluid flowing from the bark of the myrrh tree belonging to the myrrh family, and its medicinal components are 25 to 35% resin, 2.5 to 9% volatile essential oil, and 57 to 65% tree resin. The myrrh has a significant anti-inflammatory and analgesic effect, inhibits skin fungi, and inhibits the development of tuberculosis bacteria. In addition, it has excellent efficacy in relieving pain while improving blood circulation, and is thus widely used to treat joint swelling, congestion caused by bruises, and arthralgia.

The composition according to the present disclosure contains as active ingredients *Angelica gigas, Cnidium officinale, Phlomis umbrosa, astragalus* membranceus, *Amomi fructus, Citri unshius pericarpium, Drynariae Rhizoma, Codonopsis Pilosulae Radix*, frankincense, and myrrh, and may contain at least one auxiliary ingredient, such as, for example, atractylodes rhizome, hawthorn, malt, paeonia japonica, eucommia, corydaline, hyssop, acanthopanax, quince, the fruit of the Chinese matrimony vine, licorice, dioscoreae rhizoma, Cornus fruit, and dried rehmannia glutinosa.

According to one embodiment of the present disclosure, the method for manufacturing a composition promoting recovery from a bone fracture includes preparing a mixture of *Angelica gigas, Cnidium officinale, Phlomis umbrosa, astragalus* membranceus, *Amomi fructus, Citri unshius pericarpium, Drynariae rhizoma, Codonopsis Pilosulae Radix*, frankincense and myrrh, and aging the mixture.

According to one embodiment of the present disclosure, the aging of the mixture includes adding 5-10 parts by weight of rice spent water to the mixture and aging the mixture at a temperature of 40° ° C. for 10 hours.

The aging of the mixture with 5-10 parts by weight of rice spent water added eliminates or reduces the toxicity, irritation and side effects of the mixture containing *Angelica gigas, Cnidium officinale, Phlomis umbrosa, astragalus* membranceus, *Amomi fructus, Citri unshius pericarpium, Drynariae Rhizoma, Codonopsis Pilosulae Radix*, frankincense, and myrrh, enhances the medicinal effects, and helps subsequent powdering. In particular, adding 5-10 parts by weight of rice spent water to the mixture and aging the mixture at 40° C. for 10 hours facilitates the extraction of the active ingredients contained in the mixture and reduces the bitterness of the mixture, thereby allowing the mixture to be easily consumed by users of different ages.

According to one embodiment of the present disclosure, the method for manufacturing a composition promoting recovery from a bone fracture includes smoking the mixture.

According to one embodiment of the present disclosure, the smoking of the mixture includes smoking the mixture at a temperature of 80° ° C. for 2 hours using smoke from burning 5-10 parts by weight of cherry wood.

The smoking of the mixture using smoke from burning 5-10 parts by weight of cherry wood imparts the sweetness of the cherry wood smoke to the mixture, reducing bitterness and providing flavor for use of the mixture as a food or medicinal product.

A method for manufacturing a composition promoting recovery of a bone fracture according to one embodiment of the present disclosure includes drying the mixture and grinding the same into a powder.

The mixture according to the present disclosure is dried at 90° C. and ground into a powder with a particle size of 0.1-0.5 cm.

The method for manufacturing a composition promoting recovery of a bone fracture according to one embodiment of the present disclosure includes extracting a liquid from the powder.

According to one embodiment of the present disclosure, the extracting of the liquid from the powder includes adding 5-10 parts by weight of ethanol to the powder as a solvent, and repeatedly extracting the liquid 6 times at a temperature of 60° C. for 2 hours by applying a 20-30 kHz ultrasonic wave.

The ultrasonic extraction according to the present disclosure generates very large energy by cavitation caused by ultrasonic vibration. In addition, due to the local temperature, sufficient energy is obtained to increase the kinetic energy of the reactant particles located in the vicinity, and high pressure is induced by the impact effect of the ultrasonic energy to enhance the mixing and extraction effect (Chung et al., 2000).

The ultrasonic extraction process may shorten the extraction time, improve the extraction yield, and ensure the safe elution of useful components. The high pressure caused by the cavitation generated by the ultrasonic energy may not only shorten the travel distance of the fatty substance by destroying the cellular tissue, but also facilitate diffusion by the stirring effect caused by the creation and destruction of cavities, resulting in a high extraction amount in a shorter time than in conventional extraction methods.

The ultrasonic extraction according to the present disclosure is performed by adding 5-10 parts by weight of ethanol as a solvent to the powder using an ultrasonic homogenizer (KUS-650, KBT, Seongnam, Korea) and generating 20-30 KHz ultrasonic waves at a temperature of 60° C. for a total of 2 hours, by repeating the process of 10 minutes of extraction and 10 minutes of rest 6 times.

The ultrasonic extraction according to the present disclosure is performed by a system capable of ensuring human safety and performing selective extraction, and provides the effect of uniform and efficient extraction of the active ingredients of the composition. The unique ingredients are nutritionally stable and can be preserved for a long time.

The present invention will be described in more detail below with reference to embodiments of the present disclosure. However, it should be noted that these embodiments are intended to illustrate the present invention, and the present invention is not limited by these embodiments.

Embodiment 1

To manufacture the composition promoting recovery from a bone fracture according to the present disclosure, 12 parts by weight of *Angelica gigas*, 12 parts by weight of *Cnidium officinale*, 6 parts by weight of *Phlomis umbrosa*, 12 parts by weight of *astragalus membranceus*, and 7 parts by weight of *Amomi fructus*, 7 parts by weight of *Citri unshius pericarpium*, 7 parts by weight of *Drynariae Rhizoma*, 3 parts by weight of *Codonopsis Pilosulae Radix*, 3 parts by weight of frankincense, and 3 parts by weight of myrrh are mixed, and 7 parts by weight of rice spent water are added to the mixture. Then, the mixture is aged at 40° C. for 10 hours.

The mixture is smoked at a temperature of 80° C. for 2 hours using smoke from burning 7 parts by weight of cherry wood, and the smoked mixture is dried at a temperature of 90° C., and then ground into a powder with a particle size of 0.3 cm.

7 parts by weight of ethanol was added to the powder as a solvent, and 25 kHz ultrasonic waves were generated using the ultrasonic homogenizer (KUS-650, KBT, Seongnam, Korea) at a temperature of 60° C. for 2 hours with 6 repetitions of 10 minutes of extraction and 10 minutes of rest to obtain a composition that promotes recovery from a bone fracture.

Comparative Example 1

A nutritional supplement that promotes recovery from bone fractures using commercially available oriental herbal medicines was used.

Comparative Example 2

The composition was manufactured in the same manner as in Embodiment 1, except that instead of adding 7 parts by weight of rice spent water to the mixture, aging the mixture at 40° C. for 10 hours, and smoking the mixture at 80° C. for 2 hours using smoke from burning 7 parts by weight of cherry wood, the mixture was smoked at 80° C. for 2 hours using smoke from burning 7 parts by weight of cherry wood, without adding 7 parts by weight of rice spent water to the mixture and aging the mixture at 40° C. for 10 hours.

Comparative Example 3

The composition was manufactured in the same manner as in Embodiment 1, except that instead of preparing the powder by adding 7 parts by weight of rice spent water to the mixture, aging the mixture at 40° C. for 10 hours, and smoking the mixture at 80° C. for 2 hours using smoke from burning 7 parts by weight of cherry wood, the mixture was aged at 40° ° C. for 10 hours with 7 parts by weight of rice spent water added, and was then dried and ground into a powder.

Comparative Example 4

The composition was manufactured in the same manner as in Embodiment 1, except that instead of by adding 7 parts by weight of rice spent water to the mixture, aging the mixture at 40° C. for 10 hours, and smoking the mixture at 80° C. for 2 hours using smoke from burning 7 parts by weight of cherry wood, the mixture was aged at 40° C. for 10 hours with 1 part by weight of rice spent water added, and was then smoked at 80° C. for 2 hours using smoke from burning 7 parts by weight of cherry wood.

Comparative Example 5

The composition was manufactured in the same manner as in Embodiment 1, except that instead of by adding 7 parts by weight of rice spent water to the mixture, aging the mixture at 40° C. for 10 hours, and smoking the mixture at 80° C. for 2 hours using smoke from burning 7 parts by weight of cherry wood, the mixture was aged at 40° C. for 10 hours with 30 parts by weight of rice spent water added, and was then smoked at 80° ° C. for 2 hours using smoke from burning 7 parts by weight of cherry wood.

Comparative Example 6

The composition was manufactured in the same manner as in Embodiment 1, except that instead of by adding 7 parts by weight of rice spent water to the mixture, aging the mixture at 40° ° C. for 10 hours, and smoking the mixture at 80° ° C. for 2 hours using smoke from burning 7 parts by weight of cherry wood, the mixture was aged at 40° C. for 10 hours with 7 parts by weight of rice spent water added, and was then smoked at 80° C. for 2 hours using smoke from burning 1 part by weight of cherry wood.

Comparative Example 7

The composition was manufactured in the same manner as in Embodiment 1, except that instead of by adding 7 parts by weight of rice spent water to the mixture, aging the mixture at 40° ° C. for 10 hours, and smoking the mixture at 80° C. for 2 hours using smoke from burning 7 parts by weight of cherry wood, the mixture was aged at 40° C. for 10 hours with 7 parts by weight of rice spent water added, and was then smoked at 80° C. for 2 hours using smoke from burning 30 parts by weight of cherry wood.

Experimental Example 1: Osteoblast Proliferation Test

For Embodiment 1 and Comparative examples 1 to 7, the differentiation activity of osteoblasts in response to the composition promoting recovery from bone fracture was measured.

To test the bony recovery for the composition promoting recovery from bone fracture for Embodiment 1 and Comparative examples 1 to 7, osteoblasts (MC3T3-E1) were seeded into 96 wells at $5 \times 10^3$ cells/100 ul and stabilized for 24 hours. For Embodiment 1 and Comparative examples 1 to 7, the cells were incubated in a $CO_2$ incubator for 48 hours. After the incubation, the cells were treated with MTT (EZ-cytox, Daillab) solution and analyzed with a microplate reader (Epoch, Biotek) at 450 nm wavelength after 2 hours of $CO_2$ incubation. The results are shown in Table 1 below.

TABLE 1

| Results of osteoblast proliferation measurements | |
| --- | --- |
| | Cell proliferation (%) |
| Embodiment 1 | 144 |
| Comparative example 1 | 100 |
| Comparative example 2 | 121 |
| Comparative example 3 | 120 |
| Comparative example 4 | 126 |
| Comparative example 5 | 128 |
| Comparative example 6 | 132 |
| Comparative example 7 | 131 |

Based on the results in Table 1 above, it can be seen that the composition promoting recovery from the bone fracture of Embodiment 1 provides a higher increase in bone recovery than the products of Comparative examples 1 to 7.

More specifically, in the case of Embodiment 1, it was confirmed that the bone recovery was promoted more than in Comparative examples 1 and 7 by adding 7 parts by weight of rice spent water to the mixture, aging the mixture at 40° C. for 10 hours, and smoking the mixture at 80° ° C. for 2 hours using smoke from burning 7 parts by weight of cherry wood. It was confirmed that the composition was effective in promoting recovery from bone fractures because the active ingredients contained in the composition were extracted uniformly and efficiently when the mixture was prepared by adding 7 parts by weight of rice spent water, aged, and smoked with smoke from burning 7 parts by weight of cherry wood.

Experimental Example 2: Bone Regeneration Induction Test

To test the induction of bone regeneration for the composition promoting recovery from bone fracture for Embodiment 1 and Comparative examples 1 to 7, a micro-CT (μCT) analysis of the extent of bone formation was performed when skull-deficient mice were treated with the composition. The results are shown in Table 2 below.

TABLE 2

| Results of bone regeneration induction measurements | |
| --- | --- |
| | Extent of bone formation |
| Embodiment 1 | +++++ |
| Comparative example 1 | + |

TABLE 2-continued

| Results of bone regeneration induction measurements | |
| --- | --- |
| | Extent of bone formation |
| Comparative example 2 | ++ |
| Comparative example 3 | ++ |
| Comparative example 4 | +++ |
| Comparative example 5 | +++ |
| Comparative example 6 | +++ |
| Comparative example 7 | +++ |

Based on the results in Table 2 above, it can be seen that the composition promoting recovery from bone fracture of Embodiment 1 provides higher induction of bone regeneration than the products of Comparative examples 1 to 7.

More specifically, in the case of Embodiment 1, it was confirmed that the induction of bone regeneration was higher than in Comparative examples 1 and 7 by adding 7 parts by weight of rice spent water to the mixture, aging the mixture at 40° ° C. for 10 hours, and smoking the mixture at 80° C. for 2 hours using smoke from burning 7 parts by weight of cherry wood. In particular, it was confirmed that aging and smoking the mixture was effective in inducing bone regeneration because the extraction yield of the active ingredients of the composition was increased and impurities were removed.

Experimental Example 3: Sensory Test

Sensory tests regarding taste, aroma, and overall palatability of the composition promoting recovery from bone fracture were conducted for Embodiment 1 and Comparative examples 1 to 7. The sensory test was performed by 30 sensory testers (15 men and 15 women) with experience in sensory testing, using a 9-point scale. The results are shown in Table 3 below.

TABLE 3

| Results of sensory test | | | |
| --- | --- | --- | --- |
| | Taste | Aroma | Overall palatability |
| Embodiment 1 | 8.8 | 8.5 | 8.4 |
| Comparative example 1 | 5.0 | 5.0 | 5.0 |
| Comparative example 2 | 6.4 | 6.5 | 6.7 |
| Comparative example 3 | 6.6 | 6.4 | 6.8 |
| Comparative example 4 | 7.5 | 7.2 | 7.4 |
| Comparative example 5 | 7.8 | 7.4 | 7.3 |
| Comparative example 6 | 7.6 | 7.8 | 7.6 |
| Comparative example 7 | 7.7 | 7.7 | 7.5 |

Based on the results in Table 3 above, it can be seen that the composition promoting recovery from bone fracture of Embodiment 1 provides a higher score in the sensory test than the products of Comparative examples 1 to 7.

More specifically, for Embodiment 1, it was confirmed that by adding 7 parts by weight of rice spent water to the mixture, aging the mixture at 40° C. for 10 hours, and smoking the mixture at 80° C. for 2 hours using smoke from burning 7 parts by weight of cherry wood, the mixture provided higher flavor and aroma than in Comparative examples 1 and 7. It was confirmed that adding 7 parts by weight of rice spent water to the mixture, aging the mixture, and smoking the mixture with smoke from burning 7 parts by weight of cherry wood was effective in increasing the utilization of the composition because it reduced bitterness and increased sweetness.

Compared to conventional methods for manufacturing a composition that promotes recovery from bone fractures, the method for manufacturing a composition promoting recovery from bone fractures according to one embodiment of the present disclosure may provide a composition promoting recovery from bone fractures that effectively promotes recovery from bone fractures while reducing bitterness, increasing sweetness, and improving absorption of key ingredients.

As is apparent from the above description, the present disclosure provides the following effects.

A method for manufacturing a composition promoting recovery from a bone fracture according to the present disclosure may provide a composition capable of treating the bone fracture.

A method for manufacturing a composition promoting recovery from a bone fracture according to the present disclosure may provide a composition capable of promoting bone growth.

A method for manufacturing a composition promoting recovery from a bone fracture according to the present disclosure may provide a composition that can be consumed by various age groups.

A method for manufacturing a composition promoting recovery from a bone fracture according to the present disclosure may provide a composition that can be used as a main ingredient or added as a minor ingredient in the fields of medicine, cooking, nutritional products, and the like.

The effects of the present disclosure are not limited to those mentioned above, and other effects not mentioned will be apparent to those skilled in the art from the claims.

The foregoing description of the disclosure is provided to enable those skilled in the art to practice or use the disclosure. Various modifications of the disclosure will be readily apparent to those skilled in the art, and the general principles defined herein may be applied to various modifications without departing from the spirit or scope of the disclosure. Accordingly, the disclosure is not intended to be limited to the examples described herein, but is intended to be given the broadest possible scope consistent with the principles and novel features disclosed herein.

While the present disclosure has been described in relation to some embodiments, it should be appreciated that various modifications and changes can be made without departing from the scope of the present disclosure as would be understood by one of ordinary skill in the art to which the present disclosure pertains. Further, such modifications and changes are to be considered as falling within the scope of the claims appended hereto.

What is claimed is:

1. A method for manufacturing a composition for promoting recovery from a bone fracture, the method comprising:

preparing a mixture of *Angelica gigas, Cnidium officinale, Phlomis umbrosa, Astragalus membranceus, Amomi fructus, Citri unshius pericarpium, Drynariae rhizome, Codonopsis pilosula radix*, frankincense, and myrrh;

adding 5-10 parts by weight of a rice spent water to the mixture and aging the resulting mixture at a temperature of 40° C. for 10 hours;

smoking the aged mixture with smoke from burning 5-10 parts by weight of a cherry wood at a temperature of 80° C. for 2 hours;

drying the smoked mixture and grinding the dried mixture into a powder; and extracting the powder with a liquid to obtain said composition for promoting recovery from a bone fracture, comprising adding 5-10 parts by weight of ethanol to the powder as a solvent and applying thereto 20-30 kHz ultrasonic waves 6 times at a temperature of 60° C. for 2 hours.

2. The method of claim 1, wherein the composition comprises 10-15 parts by weight of *Angelica gigas,* 10-15 parts by weight of *Cnidium officinale,* 5-7 parts by weight of *Phlomis umbrosa,* 10-15 parts by weight of *Astragalus membranceus,* 15-0 parts by weight of *Amomi fructus,* 5-10 parts by weight of *Citri unshius pericarpium,* 5-10 parts by weight of *Drynariae rhizome,* 1-5 parts by weight of *Codonopsis pilosula radix,* 1-5 parts by weight of frankincense, and 1-5 parts by weight of myrrh.

3. The method of claim 1, wherein the adding step comprises adding 7 parts by weight of the rice spent water to the mixture.

4. The method of claim 1, wherein the smoking of the aged mixture comprises burning 7 parts by weight of the cherry wood.

* * * * *